United States Patent [19]

Miyashita et al.

[11] Patent Number: 5,412,217
[45] Date of Patent: May 2, 1995

[54] DENSITY-MOISTURE MEASURING APPARATUS

[75] Inventors: Kyoichi Miyashita, Osaka; Junichi Ogawa, Tokyo, both of Japan

[73] Assignee: Earthnics Corporation, Tokyo, Japan

[21] Appl. No.: 828,948

[22] PCT Filed: Jun. 11, 1991

[86] PCT No.: PCT/JP91/00780
§ 371 Date: Feb. 11, 1992
§ 102(e) Date: Feb. 11, 1992

[87] PCT Pub. No.: WO91/19969
PCT Pub. Date: Dec. 26, 1991

[30] Foreign Application Priority Data

Jun. 13, 1990 [JP] Japan ................... 2-156363

[51] Int. Cl.$^6$ .......................... G01T 3/06; G01N 23.09
[52] U.S. Cl. ............................. 250/390.05; 250/367; 250/390.11
[58] Field of Search ........... 250/390.05, 390.11, 250/390.07, 367

[56] References Cited

U.S. PATENT DOCUMENTS

| | | | |
|---|---|---|---|
| H590 | 2/1989 | Chiles et al. | 250/367 |
| 2,910,592 | 10/1959 | Armstead | 250/367 |
| 3,786,253 | 1/1974 | Haffner et al. | |
| 3,988,586 | 10/1976 | Stuart et al. | 250/390.11 |
| 4,439,675 | 3/1984 | Campbell | 250/390.05 |
| 4,884,288 | 11/1989 | Sowerby | 250/390.05 |

FOREIGN PATENT DOCUMENTS

| | | | |
|---|---|---|---|
| 61-71341 | 9/1984 | Japan. | |
| 74890 | 3/1990 | Japan | 250/367 |

OTHER PUBLICATIONS

Hiroshi Tominaga et al., "Simultaneous Utilization of Neutrons and γ-rays from $^{252}$Cf for Measurement of Moisture and Density", Int. J. Appl. Radiat. Isot., vol. 34, No. 1, pp. 429–436, 1983.

Primary Examiner—Carolyn E. Fields
Attorney, Agent, or Firm—Lowe, Price, LeBlanc & Becker

[57] ABSTRACT

A density-moisture measuring apparatus includes an NaI scintillator 4 which detects only a gamma ray from a californium 1 which has passed through an object 20, a plastic scintillator 15 for detecting the gamma ray and a fast neutron ray, and a photomultiplier 6 coupled to these scintillators. It can be said that there is a proportional relation between gamma ray data Nc and Nγ which have passed through the object 20 detected by the NaI scintillator 4 and the plastic scintillator 15. The gamma ray data and the fast neutron ray data Nγ and Nn detected by plastic scintillator 15 are not separated from each other even by a pulse-shape discrimination, but they can be separated by using a relation between gamma ray data Nc detected by the NaI scintillator 4 and the gamma ray data detected by the plastic scintillator 15. Further, since a plastic scintillator 15 is used, handling is easy. In addition, plastic scintillator detects the gamma ray and the fast neutron ray and it also serves as an optical guide of the detected light from the NaI scintillator.

12 Claims, 10 Drawing Sheets

FIG. 6

DENSITY-MOISTURE MEASURING APPARATUS

TECHNICAL FIELD

The present invention relates to a density-moisture measuring apparatus for simultaneously measuring density and moisture content by using gamma ray and fast neutron ray and, more specifically to a density-moisture measuring apparatus allowing easy handling and analysis.

BACKGROUND ART

Various methods of simultaneously measuring moisture and density of various materials have been proposed. In a widely used sampling method, data differs when samples are taken from different parts, and the results cannot be immediately known. Therefore, simultaneous measurement of density and moisture continuously in on-line manner, instead of the aforementioned sampling method, has been suggested. One example of such method is shown in, for example, FIG. 1.

Figure 1:
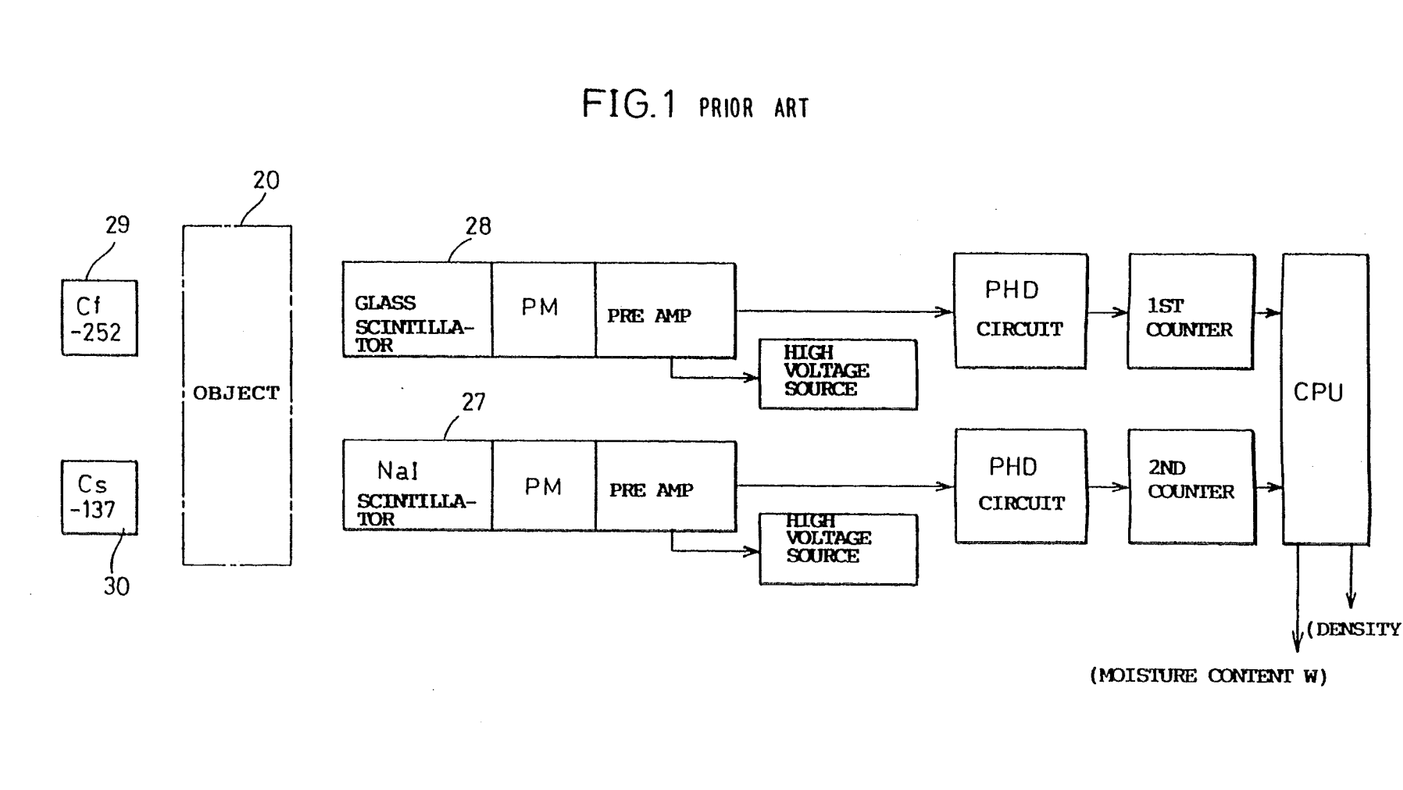
FIG. 1 is a block diagram of a conventional apparatus for measuring density and moisture on-line.

Referring to FIG. 1, in an on-line measuring apparatus for measuring a bulk material, a first radiation source 29 (for example Cf-252) and a second radiation source 30 (for example Cs-137) are provided on the way of feeding of the object (for example, coke) on a belt conveyer. Radioactive rays emitted from the first and second radiation sources 29 and 30 and passed through the object 20 are detected by a detector. In order to measure simultaneously the density and the moisture content of object 20 on-line, it was necessary to provide in the detector a density meter 27 formed of an NaI scintillator, for example for detecting gamma ray, and a moisture meter 28 formed of a glass scintillator, for example, for detecting fast neutron ray. Outputs from these scintillators were separated by a pulse height discriminating circuit (PHD circuit) in accordance with a pulse height discriminating method utilizing spectral characteristics, whereby respective data of measurement were provided.

However, simultaneous measurement of one object 20 by using two different meters 27 and 28 requires much space for arranging respective meters, and maintenance of these meters is troublesome.

In order to solve these problems, use of phoswich detector including an NaI scintillator and a plastic scintillator has been proposed. An example is disclosed, for example, in Japanese Patent Laying-Open No. 2-74890.

According to this article, outputs from two different scintillators are received by a photomultiplier (hereinafter referred to as a PM) and amplified by a pulse amplifier. In this case also, a PHD circuit is used.

However, according to this method, pulse-height distribution of the gamma ray pulses detected by the NaI scintillator and that of neutron ray pulses detected by the plastic scintillator cannot be separated well dependent on the height of the pulses, which prevents stable analysis.

In order to provide stable result of analysis, use of a liquid scintillatot with pulse shape discriminating method has been proposed. Combination of a PSD (Pulse Shape Discrimination) circuit and a liquid scintillator brings about an advantage that fast neutron ray can be discriminated from gamma ray. However, a liquid scintillator is difficult to handle, since it is mechanically fragile and inflammable. In addition, practical application is difficult, except for study in laboratories, since it is very expensive.

The present invention was made to solve the above described problems, and its object is to provide a density-moisture meter allowing easy handling and easy analysis.

Another object of the present invention is to provide a density-moisture meter employing a phoswich detector which enables effective and stable measurement.

A further object of the present invention is to provide a density-moisture meter which can be applied to general field of industry.

A still further object of the present invention is to provide a method of industrial measurement of density and moisture allowing ready analysis.

DISCLOSURE OF THE INVENTION

The density-moisture measuring apparatus of the present invention includes a phoswich detector including a gamma ray scintillator and a plastic scintillator for detecting gamma ray and fast neutron ray optically coupled to one photomultiplier. The phoswich detector detects radioactive rays entering through an object of measurement. The detecting signals from phoswich detector are separated into a first signal component detected by the plastic scintillator and a second signal component detected by the NaI scintillator. The first signal component includes first data provided by fast neutron ray, and second data provided by the gamma ray. The first data and the second data are separated in accordance with the second signal component. The density and moisture content of the object of measurement are calculated based on the separated first and second data.

The gamma ray and the fast neutron ray emitted from radiation source pass through the object of measurement and are detected by the plastic scintillator, and the gamma ray is also detected by the NaI scintillator. The data detected by the plastic scintillator includes data provided by the gamma ray as well as the fast neutron ray. The gamma ray detected by the NaI scintillator is proportional to the gamma ray detected by the plastic scintillator, since they are both provided from the same object of measurement. Based on this relation, data of the gamma ray and of the fast neutron ray detected by the plastic scintillator are separated from each other. Moisture content of the object is calculated based on the data provided from the fast neutron ray, and the density of the object is calculated based on the data provided from the gamma ray.

Consequently, a density-moisture meter allowing easy handling and analysis can be provided.

In accordance with another aspect of the present invention, a method of measuring density and moisture of an object of measurement includes the steps of preparing sources emitting gamma ray and fast neutron ray, detecting the gamma ray passed through the object by an NaI scintillator, detecting the gamma ray and the fast neutron ray passed through the object by a plastic scintillator, pulse-shape discriminating, by a PSD circuit, detected signals detected by the NaI scintillator and the plastic scintillator, separating the signals detected by the plastic scintillator into two data based on the data of the gamma ray detected by the NaI scintillator, and calculating the moisture and the density of the object based on the separated gamma ray data and the fast neutron ray data.

The gamma ray data and the fast neutron ray data detected by the plastic scintillator cannot be discriminated by the pulse-shape discrimination, but the gamma ray data and the fast neutron ray data of the object can be separated, since a proportional relation exists between the gamma ray detected by the NaI scintillator and the gamma ray detected by the plastic scintillator. Consequently, a method of industrial density-moisture measurement allowing easy measurement can be provided.

BEST MODE FOR CARRYING OUT THE INVENTION

Details of the present invention will be described with reference to the appended drawings.

At first, the basic idea of the present invention is described with reference to FIGS. 2 and 3.

Figure 2:
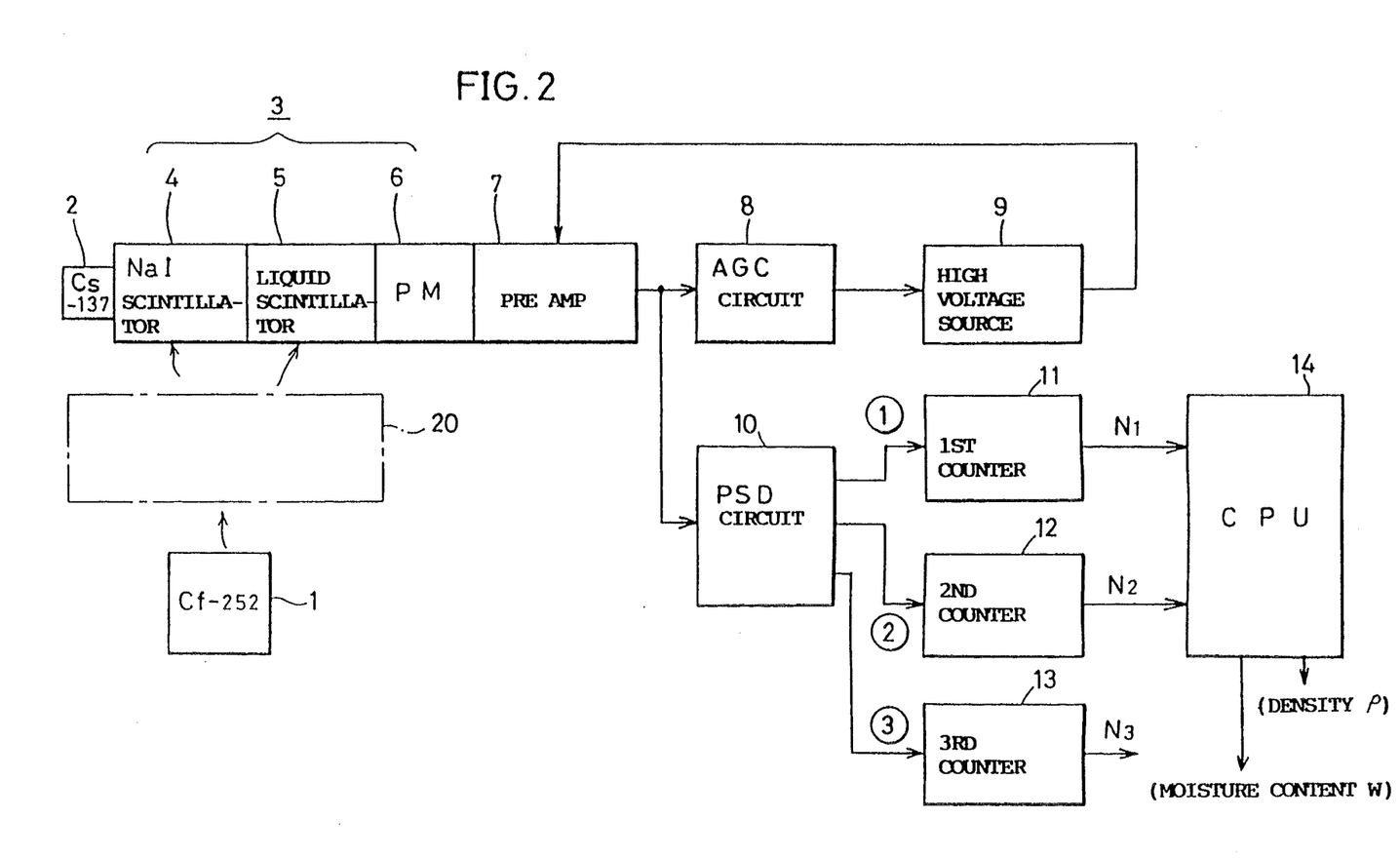
FIG. 2 is a block diagram showing a density-moisture meter employing a phoswich detector, FIG. 3 show results of wave-shape discrimination in a density-moisture measuring apparatus employing a phoswich detector.

FIG. 2 is a block diagram showing a structure of a density/moisture measuring apparatus provided by using a phoswich detector including an NaI scintillator and a liquid scintillator. Since waveform pattern of the output received by the PM of the NaI scintillator is different from that of the liquid scintillator, respective data can be provided by pulse-shaped discriminating method. An example will be described.

Referring to FIG. 2, the phoswich detector includes a first source (californium Cf-252 in this example) which passes an object 20 and radiates gamma ray and fast neutron ray, a second source (cesium 137 in this example) 2 emitting gamma ray providing a photopeak, and a phoswich detector 3 formed by an NaI scintillator 4, a liquid scintillator 5 and a PM 6. Scintillation light from NaI scintillator 4 passes through liquid scintillator 5 and enters PM 6. The first source 1 is arranged such that the radioactive ray from the first source 1 passes through an object 20 and enters both scintillators 4 and 5, while the second source 2 is arranged such that gamma ray from the second source 2 directly enters NaI scintillator 4 without passing through the object 20. Outputs from PM are amplified by a preamplifier 7 and fed to an AGC circuit 8 or to a pulse-shape discriminating circuit 10 (hereinafter referred to as a PSD circuit) for discriminating the wave shapes. AGC circuit 8 controls output voltage of a high voltage source 9 such that pulse height of the photopeak of a gamma ray detecting signal from the second source 2 included in output signals from preamplifier 7 is kept constant.

PSD circuit 10 discriminates the difference in rise time of pulses of detection signals output from preamplifier 7, and outputs pulse groups corresponding to the rise time.

Figure 3:
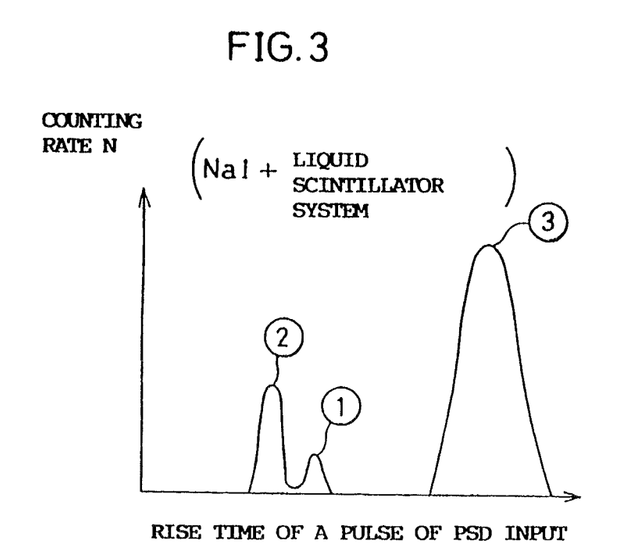

FIG. 3 is a graph showing rise time of pulses of the detection signals input to PSD circuit 10 and the distribution thereof. In the graph, reference numeral ①  denotes number of pulses (counting rate) per unit time of fast neutron ray detection detected by the liquid scintillator 5. The reference numeral ② denotes the counting rate of the gamma ray detecting pulses from the first and second sources 1, 2 detected by liquid scintillator 5. The reference numeral ③ denotes counting rate of gamma ray detecting pulses from the first and second sources 1 and 2 detected by NaI scintillator 4.

PSD circuit 10 separates ①, ② and ③ of FIG. 3 from each other, and first, second and third counters 11, 12 and 13 shown in FIG. 2 counts the number of pulses of the groups ①, ② and ③. The resulting counting rates N1, N2 and N3 are provided. The counting rate N1 is decreased corresponding to the moisture content of object 20, and counted value N2 decreases corresponding to the density of object 20. However, this value includes a prescribed counting rate of the second source 2.

A CPU 14 carries out the following arithmetic operation based on the counted values N1 and N2 to calculated moisture content W and the density $\rho$.

$N1 = N10 \exp(-\mu n \times W)$ $N2 - NS = (N20 - NS) \exp(-\mu \gamma \times \rho)$ where N10 and N20 represent counting rates when object 20 is removed (corresponding to moisture content W of 0 and density $\rho$ of 0, respectively), NS denotes contribution of the second source (2), and $\mu n$, $\mu \gamma$ are constants of the apparatus.

Although the counting rate N3 of the third counter 13 may be used for measuring the density, description thereof is omitted, since it is not related to the present discussion.

As described above, the density and the moisture content can be measured highly efficiently by the measuring apparatus employing one phoswich detector 3 which is the density/moisture measuring apparatus having the structure shown in FIG. 3. By providing signals from NaI scintillator 4 to AGC circuit 8, the gain can be stabilized.

Figure 4:
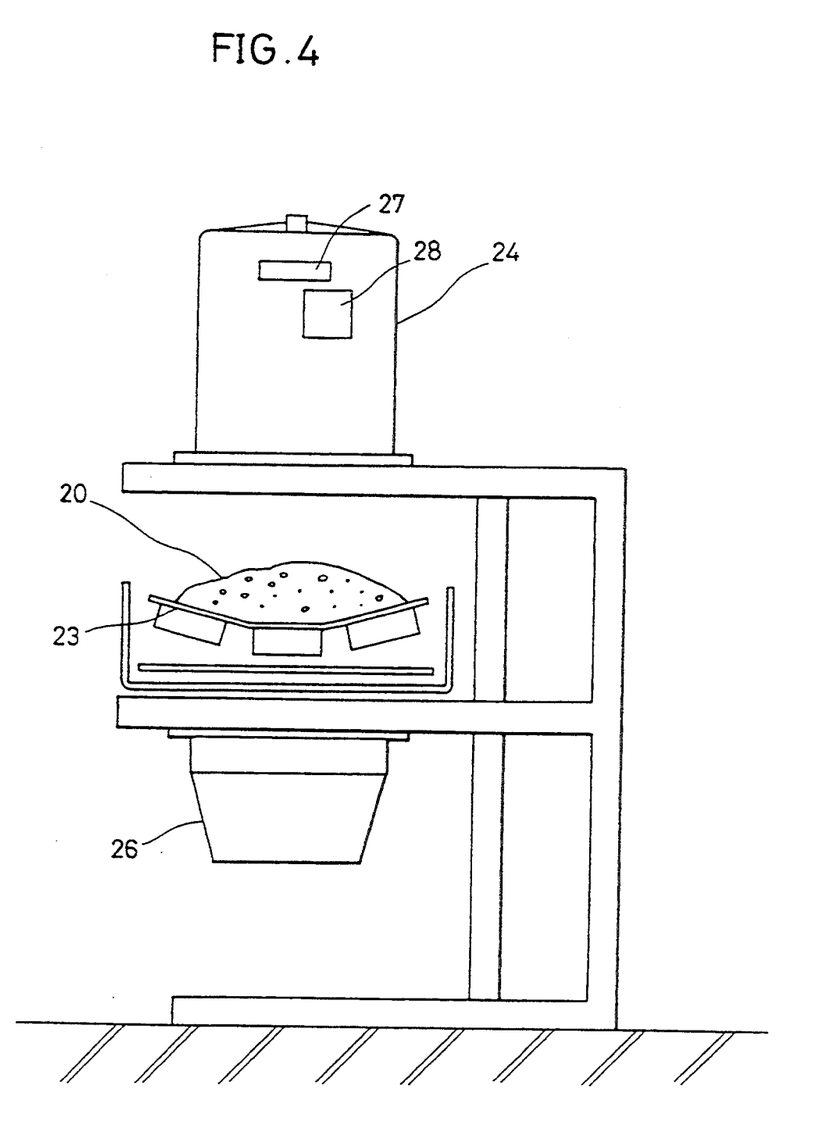
FIG. 4 shows specific arrangement of an apparatus for measuring density and moisture on-line.

FIG. 4 shows a specific arrangement of an apparatus for measuring on-line the density and moisture by using a phoswich detector in accordance with the present invention. Referring to FIG. 4, a bulky object 20 such as coke is transported on a belt conveyer 23 and the density and the moisture thereof are measured during transportation. Radioactive rays emitted from a radiation source 26 and have passed through object 20 are detected by a detecting apparatus 24. Detecting apparatus 24 includes a display portion 27 and a key setting portion 28.

Figure 5:
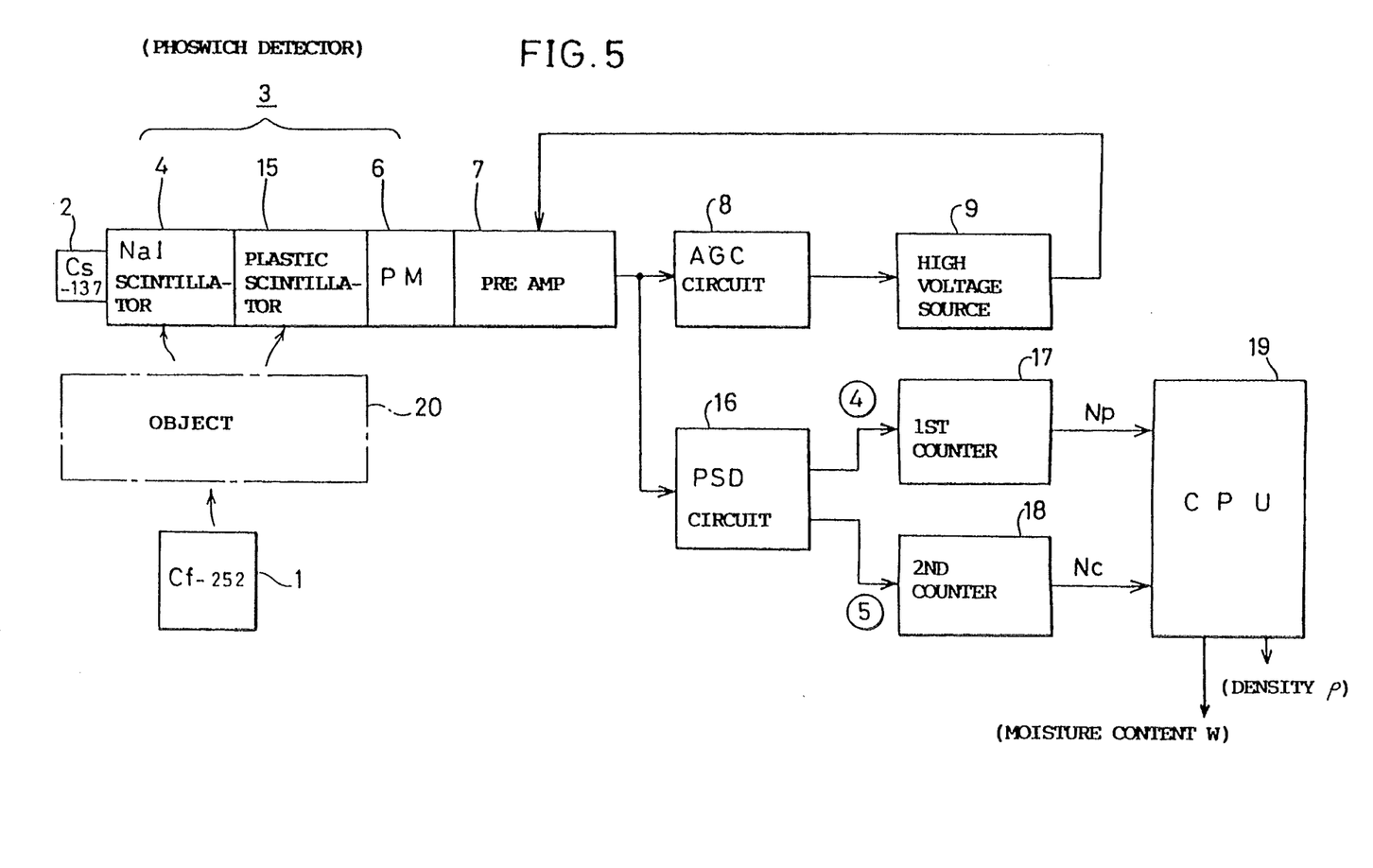
FIG. 5 is a block diagram showing a main portion of a density-moisture meter employing a phoswich detector in accordance with the present invention.
Figure 6:
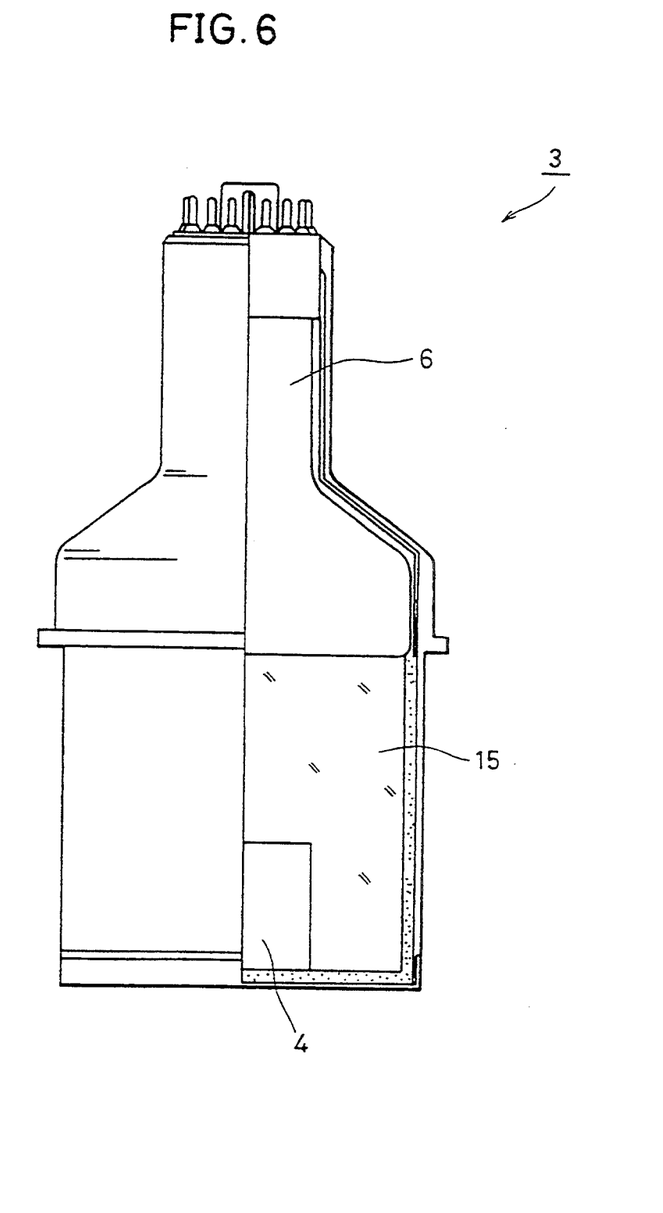
FIG. 6 is a schematic diagram showing an appearance of phoswich detector and a main portion of the density-moisture meter in accordance with the present invention.

FIG. 5 is a block diagram showing a main portion of the density-moisture measuring apparatus employing the phoswich detector in accordance with the present invention, and FIG. 6 shows an appearance of the phoswich detector 3. Referring to FIG. 5, the density-moisture measuring apparatus of the present invention has the same structure as that of FIG. 2 except that a plastic scintillator 15 is used instead of a liquid scintillator 5 in a phoswich detector 3 which is conceived from a combination shown in FIG. 2. Therefore, the same portions are denoted by the same reference characters and the detailed description thereof is not repeated. Details of the PSD circuit and of the first and second counters 17 and 18 will be described later.

A plastic scintillator can be easily processed, unlike a liquid scintillator, handling thereof is not difficult, and it is not expensive. A generally used plastic scintillator includes, for example, NE102 of Nuclear Enterprize Corporation.

Figure 7:
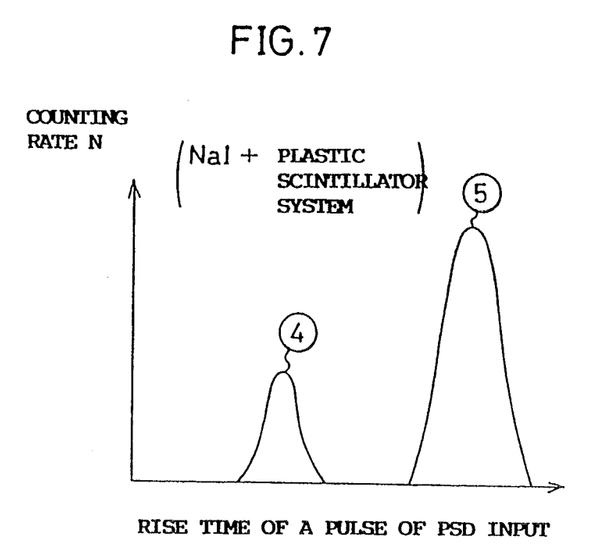
FIG. 7 shows results of wave-shape discrimination by the density-moisture meter in accordance with the present invention.

Signals detected by NaI scintillator 4 and plastic scintillator 15 and passed through PM 6 and preamplifier 7 are discriminated in PSD circuit 16. FIG. 7 shows output data from PSD circuit 16. In this graph, reference numeral ④ denotes detected signals of fast neutron ray and gamma ray from the first source 1 detected by plastic scintillator 15, and reference numeral ⑤ denotes detected signals of the gamma ray from the first source 1 and the gamma ray from the second source detected by the NaI scintillator 4.

Actually, plastic scintillator 15 also detects the gamma ray from the second source, but output from the second source is weak, and the gamma ray from the second source reaches plastic scintillator 15 after it has passed through NaI scintillator 4 so that the gamma ray is almost fully absorbed by NaI scintillator: and therefore, the detected amount of gamma ray from the second source detected by plastic scintillator 15 can be neglected.

PSD circuit 16 discriminates input signals and provides ④ and ⑤ shown in FIG. 5 to first and second counters 17 and 18. CPU 19 divides counting rate of Np of first counter 17 to a fast neutron ray counting rate Nn and a gamma ray counting rate N$\gamma$.

The method of dividing the first counting rate Np will be described.

Figure 8:
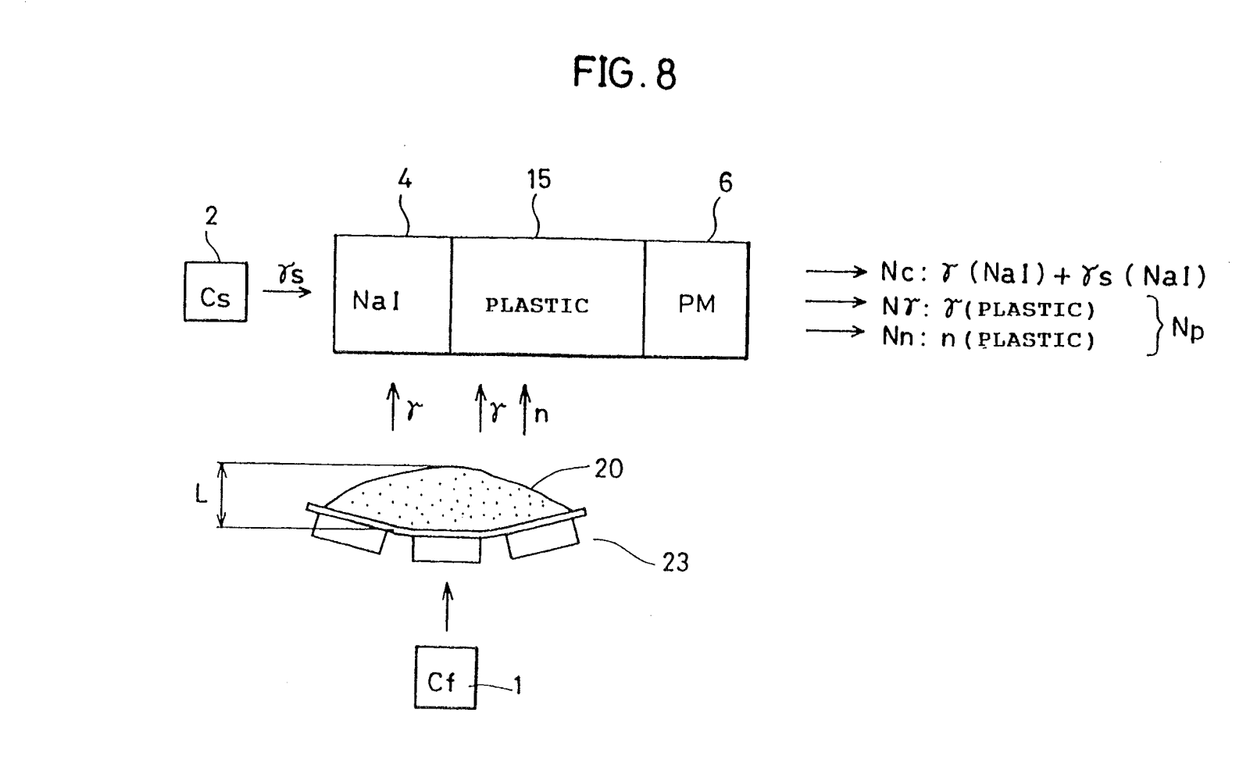
FIG. 8 illustrates the method of measurement by the density-moisture meter in accordance with the present invention.

FIG. 8 schematically shows relations among the fast neutron ray counting rate Nn and the gamma ray counting rate N$\gamma$ constituting the counting rate Np of the first counter described above, and a counting rate Nc of the second counter. The radioactive ray from the first source passes through an object 20 transported on a belt conveyor 23 and enters NaI scintillator 4 and plastic scintillator 15. NaI scintillator 4 detects only the gamma ray which has passed through the object 20, while plastic scintillator 15 detects the gamma ray as well as the fast neutron ray. The second source 2 is provided only for the AGC circuit, and for this purpose, only the signals detected by the NaI scintillator 4 are used.

The data of the gamma ray and the fast neutron ray from the object 20 detected through PM 6 under the above described conditions are as follows. The counting rate Nc detected by NaI scintillator 4 includes the gamma ray $\gamma$ (NaI) from object 20 and the gamma ray $\gamma$s (NaI) from the second source. The counting rate Np detected by plastic scintillator 15 includes the counting rate N$\gamma$ of the gamma ray from object 20 and the counting rate Nn of the fast neutron ray. The counting rate Nc detected by the NaI scintillator 4 corresponds to the detected signal represented by the reference numeral ⑤ of FIG. 7, and the counting rate Np detected by plastic scintillator 15 corresponds to the detected signal denoted by reference numeral ④ of FIG. 7.

Since the counting rate of the gamma ray $\gamma$s (NaI) from the second source is known, the value of the gamma ray $\gamma$ (NaI) from object 20 constituting the counting rate Nc of the second counter 18 can be readily known by subtracting $\gamma$s(NaI) from Nc. There is a prescribed proportional relation between the counting rate $\gamma$ (NaI) of the second counter 18 and the counting rate $\gamma$ (plastic) of the gamma ray from object 20 constituting the counting rate of the first counter 17, since both of them are provided by measuring the gamma ray which has passed through the same object 20. Therefore, in the present invention, the counting rate Np of the first counter 17 is divided into the fast neutron ray counting rate Nn and the gamma ray counting rate N$\gamma$ by making use of this relation.

Details of this division will be described in the following.

(1) Dividing method 1

In the first method of division, the counting rate of plastic scintillator 15 is measured with object 20 removed and a gamma ray source which emits the gamma ray only is provided at the position of the first source 1 in the measuring system shown in FIG. 8. Cesium Cs or cobalt Co is used as the gamma ray source.

When the counting rate of plastic scintillator 15 in this case is represented by Npo and the counting rate by NaI scintillator 4 is represented by Nco, the fast neutron ray counting rate Nn and the gamma ray counting rate N$\gamma$ can be calculated in accordance with the following equations.

$$Nc \times (Npo/Nco) = N\gamma$$

$$Np - N\gamma = Nn$$

In this case the counting rate $\gamma$s(NaI) from the second source is subtracted beforehand from the counting rate Nc.

Based on the counting rate Nn of the fast neutron ray provided in this manner, moisture content W (g/cm$^3$) per unit volume is calculated, and based on the counting ray N$\gamma$ of the gamma ray, the density $\rho$ (g/cm$^3$) of the object is calculated.

The reason is described in the following why the density is calculated besides moisture content per unit volume using the fast neutron ray. When measurement is carried out on-line by using a source while the object is transported, actually the moisture content is measured for the whole length represented by L (cm) in FIG. 8. When the unit area of the passage of the source is represented by S (cm$^2$), the moisture content WW, provided by the reaction between the fast neutron ray and hydrogen, which is actually measured, is represented by the following equation.

$$WW = W \times S \times L \text{ (g)} \qquad (1)$$

Namely, WW represents the whole moisture content of the portion through which the source passes.

Meanwhile, NaI scintillator measures the weight WM of the object represented by the following equation, based on the γ ray which has passed through the object.

$$WM = \rho \times S \times L \text{ (g)} \qquad (2)$$

From the above equations (1) and (2), the moisture content η is provided by the following equation.

$$\eta = \frac{WW}{WM} = \frac{W \times S \times L}{\rho \times S \times L} = \frac{W}{\rho}$$

From this reason, the moisture content per unit volume provided by the fast neutron ray and the density provided by the gamma ray are both measured.

(2) Dividing method 2

The second method of division in accordance with the present invention will be described. The following measuring system is prepared. The object 20 is removed and instead of plastic scintillator 15, a liquid scintillator 5 having the same size is provided in the system of FIG. 8. Since fast neutron ray and gamma ray components in plastic scintillator can be pulse-shape discriminated by the liquid scintillator, the counting rates N20 and N30 of components ② and ③ shown in FIG. 3 in this state are actually measured. Based on the result of measurement, respective data are calculated in accordance with the following equations.

$$Np \times N20/N30 = N\gamma$$

$$Np - N\gamma = Nn$$

This method of division is based on an idea that efficiency in detecting the fast neutron ray and the gamma ray of the plastic scintillator and liquid scintillator are substantially the same provided that they have the same size and the conditions of measurement are the same, since the plastic scintillator and the liquid scintillator have similar components.

(3) Method of calculating moisture percentage

The moisture content W and the density ρ can be obtained by the following calculations based on the counting rates Nn and Nγ obtained in the above-described manner.

$$Nn = Nn0 \exp(-\mu n \times W \times S \times L) \times \text{[attenuation of neutron by density]}$$

$$N\gamma = N\gamma 0 \exp(-\mu \gamma \times \rho \times S \times L)$$

where W: moisture content per unit volume of the object g/cm$^3$

ρ: density of the object, weight per unit volume g/cm$^3$

Nn0: counting rate Nn when the object is removed

Nγ0: counting rate Nγ when the object is removed

μn, μγ: apparatus constants

S: area (cm$^2$) of passage of the radioactive ray beam through the object

L: distance (cm) of passage of the same radioactive ray beam through the object Here (attenuation of neutrons by density) is not related to the gist of the invention and it may complicate the description of the present invention, so that it is omitted.

Figure 9:
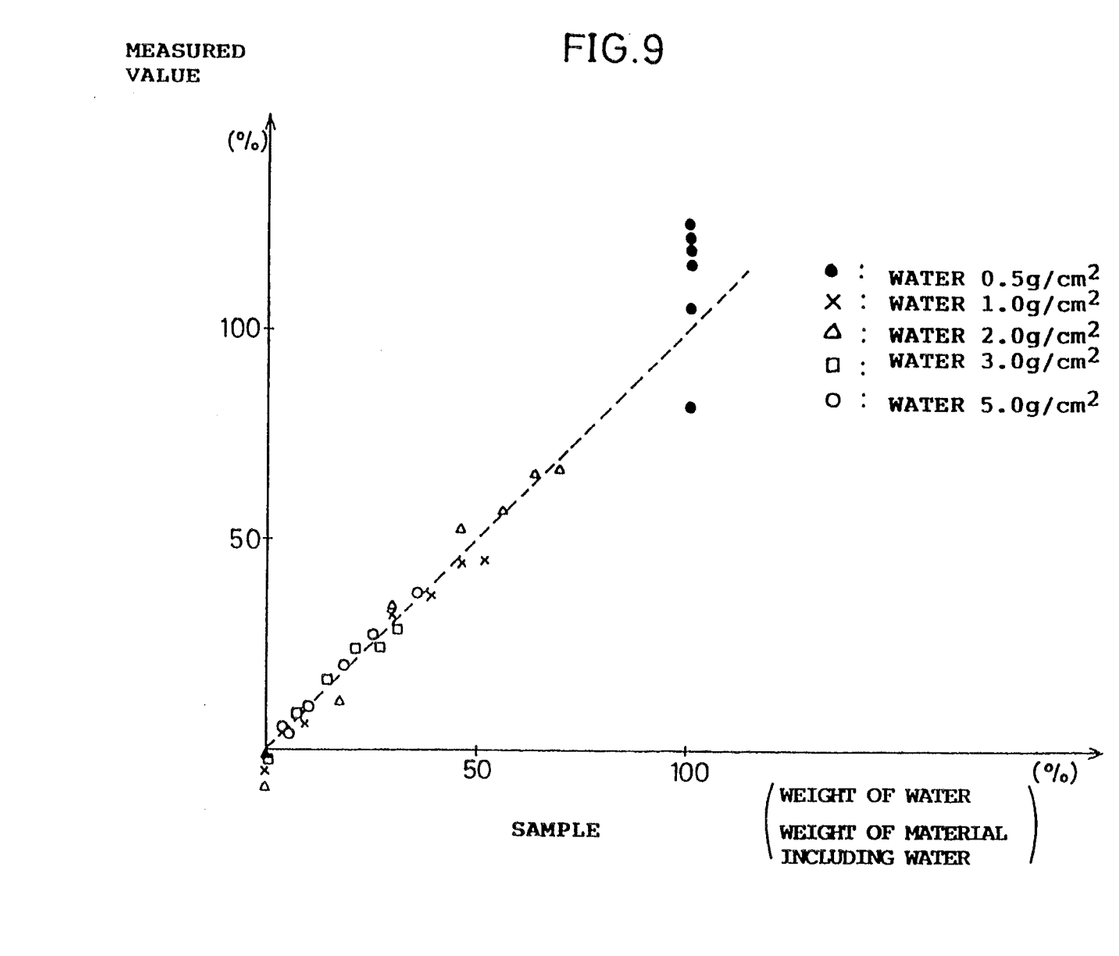
FIG. 9 shows performance of the density-moisture meter in accordance with the present invention.

FIG. 9 shows the result of measurement by the density-moisture measuring apparatus in accordance with the present invention in accordance with the above described method of distribution. FIG. 9 is a graph in which X axis denotes moisture percentage of a sample which has been known in advance, and Y axis denotes the result of measurement by the density-moisture measuring apparatus of the present invention. Referring to FIG. 9, the measured value is approximately the same as the actual value at any point in the range of moisture content per unit area of 0.5 g to 3.0 g.

Figure 10:
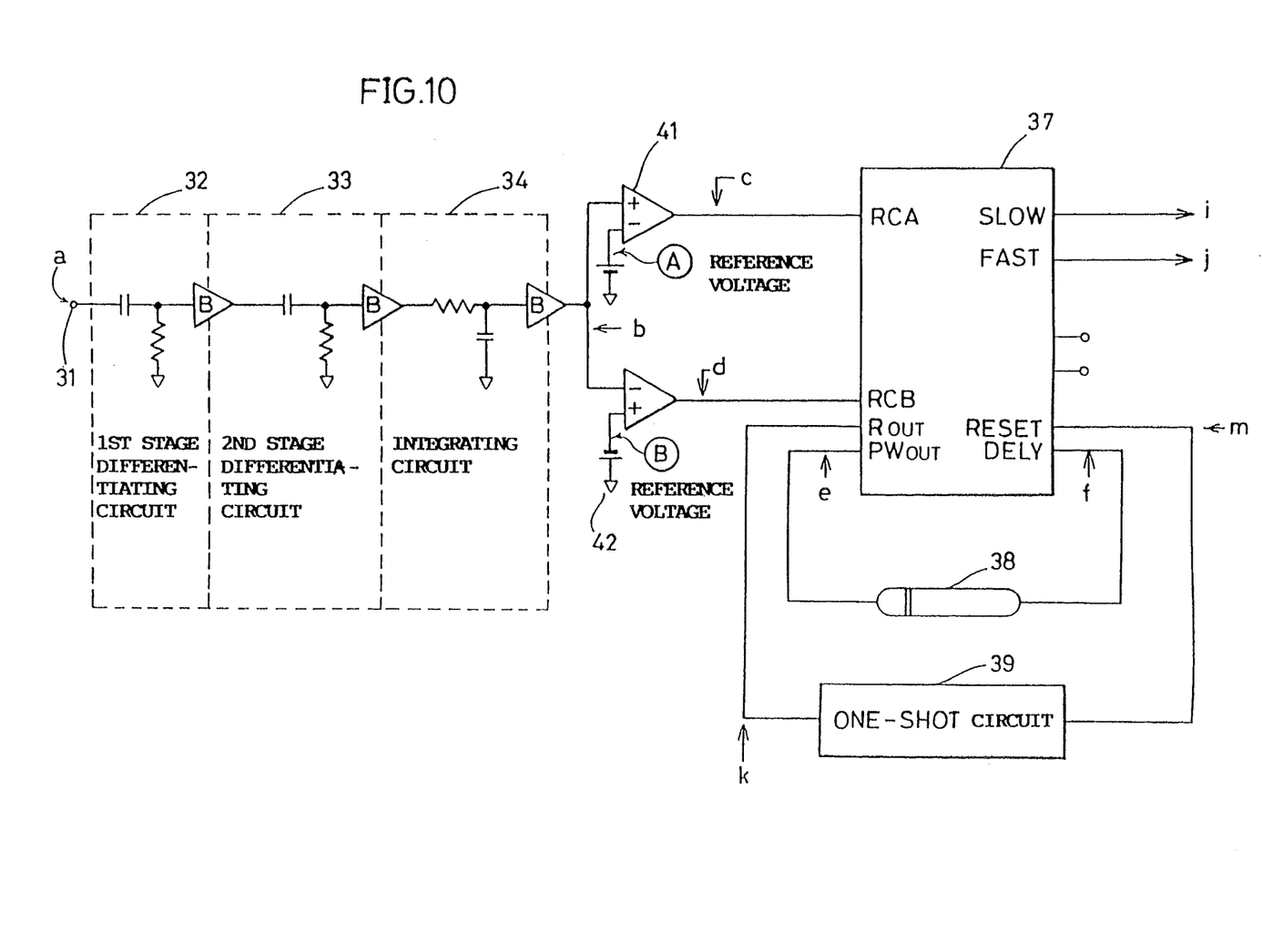
FIG. 10 is a block diagram showing a main portion of a PSD circuit.
Figure 11A:
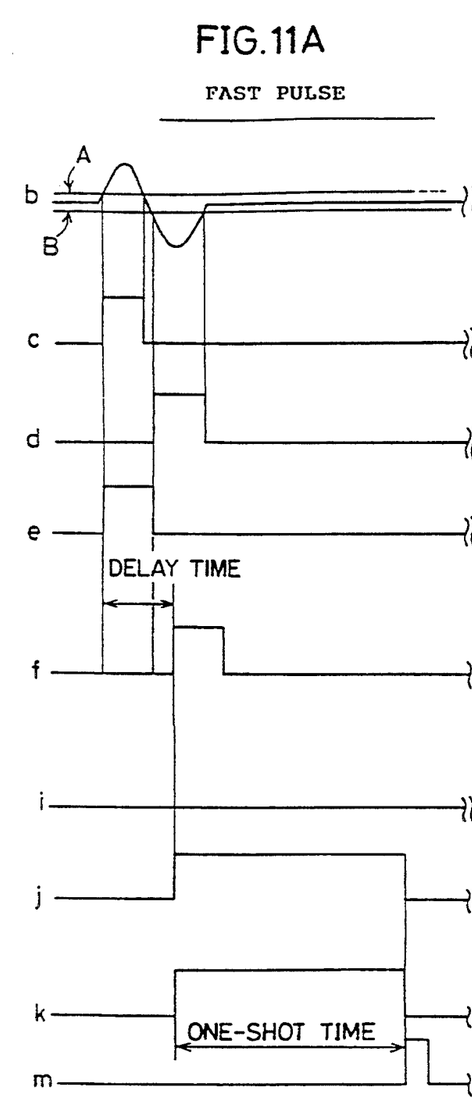
FIGS. 11A and 11B show signal waveforms at various points of the PSD circuit shown in FIG. 10.
Figure 11B:
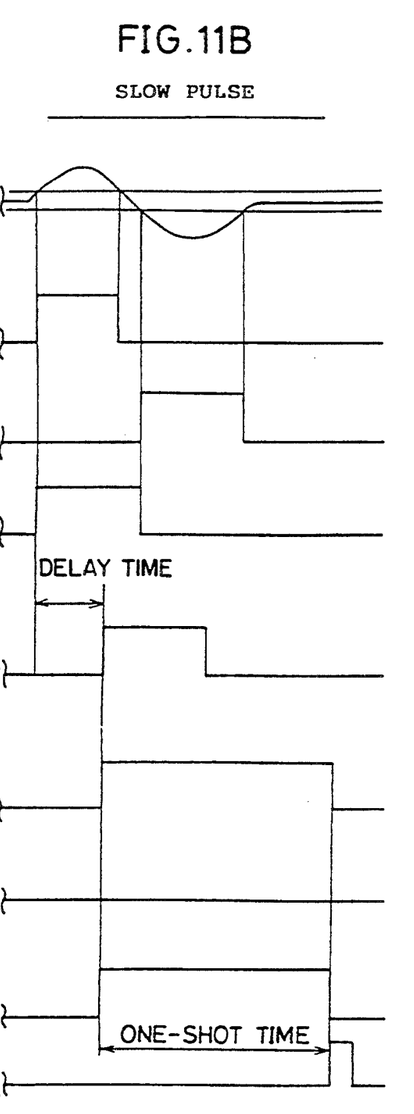

The PSD circuit used in this invention will be described. FIG. 10 is a block diagram showing a main portion of the PSD circuit, and FIGS. 11A and 11B show pulse waveforms at respective points shown in FIG. 10. FIG. 11A shows a case of a fast pulse, and FIG. 11B shows a case of a slow pulse.

A signal a is input to a PSD circuit 16 through an input terminal 31. In order to obtain a zero cross signal, signal a is differentiated twice by using a first stage differentiating circuit 32 and a second stage differentiating circuit 33, and integrated once by an integrating circuit 34, whereby a signal b is provided. Two comparators 41 and 42 are used for converting b into a pulse width. The two comparators 41 and 42 with reference voltage A applied to the side of + sign and reference voltage B applied to the side of − sign are used to provide waveforms of signals c and d, in order to avoid noises existing at the zero cross point. By using these two waveforms, a waveform of a signal e is provided by a PLD (Programmable Logic Device) 37 in accordance with the following logic equation.

Signal e = signal c*/signal d + signal e*/signal d

The pulse width of this waveform is in proportion to a rise time of the pulse, regardless of the height of the pulse.

The waveform of signal e is input to a delay line 38 to provide a waveform of a signal f. This delay time serves as a threshold value to separate pulses shorter than this from pulses longer. By changing the delay time, the threshold value for separating pulse time can be changed.

Signals i and j are provided based on the following logic equations in PLD 37 based on signals f and m.

Signal i = signal f*/signal m +/signal f* signal i*/signal m

Signal j = signal f*/signal m +/signal f* signal j* signal m

Signals i and j will be detection signals ⑤ and ④ which are input to the second counter 18 and the first counter 17 of FIG. 5.

A signal k is provided from signals i and j.

Signal k = signal i + signal j

A signal m is provided from signal k passed through a one shot circuit 39. Signal m is provided based on signal k by using one shot circuit 39, because reset is done for preparation when an earlier pulse (signal i or signal j) is detected.

In the above description, the reference character "*" denotes AND operation, "+" denotes OR operation and "/" represents negative logic.

An universal logic may be used instead of the PLD 37.

In the above-described embodiment, californium Cf-252 was used as a first source 1. However, a single source or a plurality of sources may be used provided that the fast neutron ray and the gamma ray are emitted therefrom.

Although a second source 2 was provided for operating AGC circuit 8 in order to stabilize the gain to the measuring apparatus, and if high stability is not required, the second source 2 and the AGC circuit 8 are not necessary.

Although the present invention was applied to an object 20 which is transported on a belt conveyer 23 as shown in FIG. 4 in the above described embodiment, moisture content of an object flowing through a pipe can be measured by providing a source 26 and a detector 24 on upper and lower sides of the pipe.

Although description is omitted in the foregoing, the first and second sources attenuate with inherent half lives. For example, Cf-252 attain half-value at 2.64 years and Cs-137 attains half-value at 30.0 years. For compensation, a calendar timer should preferably provided in the apparatus so as to effect reverse correction of the half life of 2.64 years of the pulse counting rate of the first source and to effect reverse correction of 30.0 years on the second source.

Applicability in Industry

As described above, according to the present invention, since a pulse-shape discriminating circuit and a phoswich detector optically coupling an NaI scintillator and a plastic scintillator to one photomultiplier is used, the density and the moisture content of an object can be efficiently and stably measured, and in addition, since a plastic scintillator which is mechanically strong is used, a density-moisture measuring apparatus which can be easily handled and inexpensive can be provided.

We claim:

1. A density-moisture measuring apparatus, comprising
    a phoswich detector including a plastic scintillator for detecting a gamma ray and a fast neutron ray and a scintillator for a gamma ray optically coupled to one photomultiplier,
    a first source arranged such that an emitted gamma ray and fast neutron ray pass through an object of measurement to enter said phoswich detector,
    first separating means for separating a detected signal from said phoswich detector into a first signal component detected by the plastic scintillator and a second signal component detected by the scintillator for the gamma ray,
    said first signal component including first data provided by said fast neutron ray and second data provided by said gamma ray,
    second separating means for separating said first data from said second data based on said second signal component, and
    calculating means for calculating density and moisture content of said object of measurement based on said first and second data separated by said second separating means.

2. The density/moisture measuring apparatus according to claim 1, wherein
    said first separating means includes pulse shape-shape discriminating means.

3. The density/moisture measuring apparatus according to claim 2, further comprising output stabilizing means for stabilizing an output from said phoswich detector.

4. A density-moisture meter for measuring on line density and moisture content of an object, comprising
    a plastic scintillator for detecting a gamma ray and a fast neutron ray,
    a scintillator for the gamma ray provided adjacent to said plastic scintillator for detecting the gamma ray only,
    a first radiation source for outputting said gamma ray and said fast neutron ray which pass through said object to enter said plastic scintillator and said scintillator for the gamma ray,
    first signal detecting means for detecting a signal detected by said plastic scintillator and integrated by the gamma ray and the fast neutron ray which have passed through said object,
    second signal detecting means for detecting a signal detected by said scintillator for the gamma ray and constituted only by the gamma ray which has passed through said object,
    separating means for separating data respectively provided by said gamma ray and said fast neutron ray detected by said first signal detecting means based on a result of detection by said second signal detecting means, and
    calculating means for calculating the density and the moisture content of said object based on said separated data.

5. The density-moisture meter according to claim 4, wherein
    said first signal detecting means and the second signal detecting means are integrated.

6. The density-moisture meter according to claim 5, further comprising output stabilizing means for stabilizing detected output from said first and second signal detecting means.

7. A density-moisture measuring method, comprising the steps of
    (a) preparing a first source emitting a gamma ray and a fast neutron ray which pass through an object of measurement,
    (b) detecting said gamma ray and the fast neutron ray which has passed through said object by using a plastic scintillator,
    (c) detecting only the gamma ray which has passed through said object by using a scintillator for the gamma ray,
    (d) pulse-shape discriminating the gamma ray and the fast neutron ray detected by said plastic scintillator and the gamma ray detected by the scintillator for the gamma ray,
    (e) data of the gamma ray and the fast neutron ray detected by said plastic scintillator kept unseparated by said pulse-shape discrimination,
    (f) separating integrated data of the gamma ray and the fast neutron ray based on the gamma ray data detected by said scintillator for the gamma ray, and
    (g) measuring the density and the moisture of said object based on the separated integrated data.

8. The density-moisture measuring method according to claim 7, further comprising the step of stabilizing detected output of the gamma ray and the fast neutron ray by said plastic scintillator and by said scintillator for the gamma ray.

9. A density/moisture measuring apparatus, comprising
    a phoswich detector including a plastic scintillator for detecting a gamma ray and a fast neutron ray and a scintillator for a gamma ray optically coupled to one photomultiplier,
    a first source arranged such that an emitted gamma ray and fast neutron ray pass through an object of measurement to enter said phoswich detector,
    first separating means for separating a detected signal from said phoswich detector into a first signal component detected by the plastic scintillator and a second signal component detected by the scintillator for the gamma ray, said first signal component including first data provided by said fast neutron ray and second data provided by said gamma ray, second separating means for separating said first data from said second data based on said second signal component, calculating means for calculating density and moisture content of said object of measurement based on said first and second data separated by said second separating means, and output stabilizing means for stabilizing an input from said first separating means, wherein said separating means includes pulse-shape discriminating means, and said stabilizing means includes an AGC circuit and a second source provided adjacent to said phoswich detector for operating said AGC circuit.

10. A density/moisture meter for measuring on line density and moisture content of an object, comprising a plastic scintillator for detecting a gamma ray and a fast neutron ray, a scintillator for the gamma ray provided adjacent to said plastic scintillator for detecting the gamma ray only, a first radiation source for outputting said gamma ray and said fast neutron ray which pass through said object to enter said plastic scintillator and said scintillator for the gamma ray, first signal detecting means for detecting a signal detected by said plastic scintillator and integrated by the gamma ray and the fast neutron ray which have passed through said object, second signal detecting means for detecting a signal detected by said scintillator for the gamma ray and constituted only by the gamma ray which has passed through said object, separating means for separating data respectively provided by said gamma ray and said fast neutron ray detected by said first signal detecting means based on a result of detection by said second signal detecting means, calculating means for calculating the density and the moisture content of said object based on said separated data, and output stabilizing means for stabilizing detected output from said first and second signal detecting means, wherein said first signal detecting means and the second signal detecting means are integrated, and said output stabilizing means includes an AGC circuit and a second radiation source provided adjacent to said scintillator for the gamma ray for operating said AGC circuit.

11. A density/moisture measuring method, comprising the steps of (a) preparing a first source emitting a gamma ray and a fast neutron ray which pass through an object of measurement, (b) detecting said gamma ray and the fast neutron ray which has passed through said object by using a plastic scintillator, (c) detecting only the gamma ray which has passed through said object by using a scintillator for the gamma ray, (d) pulse-shape discriminating the gamma ray and the fast neutron ray detected by said plastic scintillator and the gamma ray detected by the scintillator for the gamma ray, (e) data of the gamma ray and the fast neutron ray detected by said plastic scintillator kept unseparated by said pulse-shape discrimination, (f) separating integrated data of the gamma ray and the fast neutron ray based on the gamma ray data detected by said scintillator for the gamma ray, and (g) measuring the density and the moisture of said object based on the separated integrated data, wherein said separating step further includes the steps of preparing a second source outputting the gamma ray only as said first source, repeating said steps (b) to (d), and comparing an output of the gamma ray from said second source by said plastic scintillator and said scintillator for the gamma ray.

12. A density/moisture measuring method, comprising the steps of (a) preparing a first source emitting a gamma ray and a fast neutron ray which pass through an object of measurement, (b) detecting said gamma ray and the fast neutron ray which has passed through said object by using a plastic scintillator, (c) detecting only the gamma ray which has passed through said object by using a scintillator for the gamma ray, (d) pulse-shape discriminating the gamma ray and the fast neutron ray detected by said plastic scintillator and the gamma ray detected by the scintillator for the gamma ray, (e) data of the gamma ray and the fast neutron ray detected by said plastic scintillator kept unseparated by said pulse-shape discrimination, (f) separating integrated data of the gamma ray and the fast neutron ray based on the gamma ray data detected by said scintillator for the gamma ray, and (g) measuring the density and the moisture of said object based on the separated integrated data, wherein said separating step includes the steps of removing said object, replacing said plastic scintillator by a liquid scintillator having the same size, detecting the fast neutron ray and the gamma ray from said first source by said liquid scintillator for effecting another pulse-shape discrimination, and estimating rate of detection of said neutron ray and the gamma ray by said plastic scintillator based on data provided by said another pulse-shape discrimination.

* * * * *